US006958242B2

(12) United States Patent
Knezevic et al.

(10) Patent No.: US 6,958,242 B2
(45) Date of Patent: Oct. 25, 2005

(54) RAPID ASSAY, METHOD AND SYSTEM FOR DETECTING BIOWARFARE AGENTS

(75) Inventors: Vladimir Knezevic, Gaithersburg, MD (US); Dan-Paul Hartmann, Bethesda, MD (US); Jonathan Cohen, Potomac, MD (US); Elizabeth Marcus, Washington, DC (US)

(73) Assignee: 20/20/GeneSystems, Inc., Rockville, MD (US)

( * ) Notice: Subject to any disclaimer, the term of this patent is extended or adjusted under 35 U.S.C. 154(b) by 0 days.

(21) Appl. No.: 10/845,811

(22) Filed: May 14, 2004

(65) Prior Publication Data

US 2005/0148090 A1 Jul. 7, 2005

Related U.S. Application Data

(60) Division of application No. 10/371,257, filed on Feb. 21, 2003, now Pat. No. 6,770,485, which is a continuation-in-part of application No. PCT/US02/31398, filed on Oct. 2, 2002.

(60) Provisional application No. 60/388,818, filed on Jun. 14, 2002, provisional application No. 60/339,159, filed on Dec. 7, 2001, provisional application No. 60/326,930, filed on Oct. 3, 2001.

(51) Int. Cl.[7] .................... G01N 33/00; G01N 33/48
(52) U.S. Cl. .................... 436/86; 436/104; 436/164; 436/166; 436/163; 422/58; 422/61
(58) Field of Search .................... 422/58, 61; 436/86, 436/104, 166, 169, 163, 164

(56) References Cited

U.S. PATENT DOCUMENTS

| 3,992,158 | A | 11/1976 | Przybylowicz |
| 4,839,295 | A | 6/1989 | Smith |
| 5,580,794 | A | 12/1996 | Allen |
| 5,981,287 | A | 11/1999 | Sinclair et al. |
| 6,551,791 | B1 | 4/2003 | Small et al. |
| 6,562,563 | B1 | 5/2003 | Murphy et al. |

OTHER PUBLICATIONS

Jenzano et al., "Comparison of Five Techniques for the Determination of Protein Content in Mixed Human Saliva," *Analytical Biochemistry*, 159:370-376, 1986.
Pierce BCA Protein Assay Kit, product description No. 23225, pp. 1-8, copyright Aug. 2000.
Sapan et al., "Colorimetric protein assay techniques," *Biotechnol. Appl. Biochem.*, 29:99-108, 1999.
Stoscheck, "Quantitation of Protein," *Methods in Enzymology*, 182:50-68, 1990.

Primary Examiner—Lyle A. Alexander
(74) Attorney, Agent, or Firm—Klarquist Sparkman LLP

(57) ABSTRACT

Provided herein are methods for preliminary analysis of suspect samples, which can be used in triaging possible contaminated sites (e.g., sites contaminated or thought to be contaminated by biowarfare agents). In some embodiments, the methods involve testing for the presence of protein in the suspect sample; optionally, the sample can also be tested for the presence of sugar, and/or for pH determination. Specific embodiment methods are carried out in tubes or other reaction vessels, others are carried out in a pad format, and still others are carried out in a test strip format. Kits for carrying out the described methods are also provided.

23 Claims, 6 Drawing Sheets

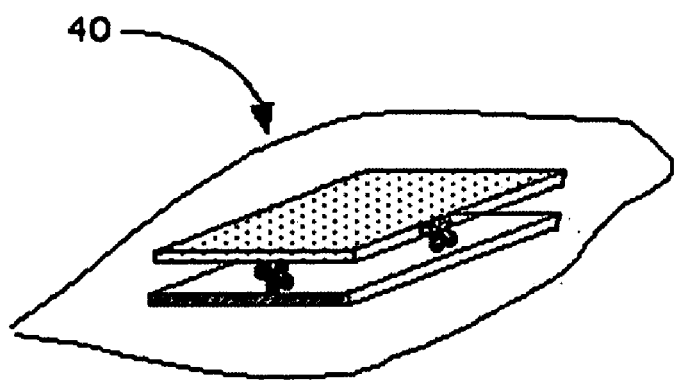
FIGURE 4
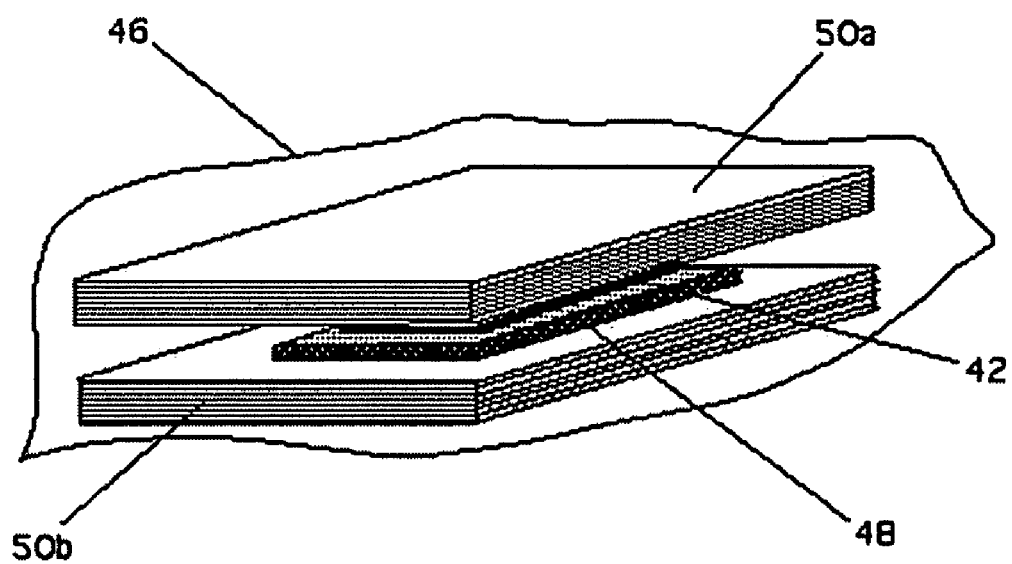

RAPID ASSAY, METHOD AND SYSTEM FOR DETECTING BIOWARFARE AGENTS

CROSS REFERENCE TO RELATED APPLICATIONS

This is a divisional application of U.S. patent application Ser. No. 10/371,257, filed Feb. 21, 2003, now U.S. Pat. No. 6,770,785, which is a continuation-in-part of International Application No. PCT/US02/31398, filed Oct. 2, 2002, which in turn claims the benefit of the following U.S. Provisional Patent Applications: 60/326,930, filed Oct. 3, 2001, 60/339,159, filed Dec. 7, 2001, and 60/388,818, filed Jun. 14, 2002. All of these applications are incorporated by reference herein in their entirety.

FIELD OF THE DISCLOSURE

This disclosure relates to methods of detecting biological material, particularly assays, methods and kits for detecting biowarfare agents such as microorganisms, biological toxins, and the like.

BACKGROUND OF THE DISCLOSURE

The bioterrorism attacks and hoaxes in the United States in the fall of 2001 placed tremendous burdens on public health and safety organizations charged with the responsibility of testing the thousands of samples that concerned citizens suspect might contain anthrax. With each confirmed case of illness from anthrax reported, thousands of calls were placed to law enforcement and emergency personnel regarding suspicious white powders and the like found in private homes, offices, restaurants, post offices, on subways, and in schools and shopping centers. Overwhelmingly these substances were found to be benign, many as mundane as pizza flour and vanilla pudding mix according to news accounts at the time. One source of many false alarms is cornstarch that is used to sort mass mailings to prevent envelopes from sticking together.

Unfortunately the anthrax scares greatly taxed the resources of health and safety personnel as each substance had to be subjected to expensive and time consuming testing in the field, a laboratory, or both. Among the techniques currently used for testing of samples suspected of containing anthrax are antibody tests, bacterial culture, and DNA testing. Each of these techniques has one or more significant limitations with respect to speed, expense, accuracy, false positives, false negatives, and/or ability to screen for multiple pathogens and toxins in parallel.

One approach currently utilized for field-testing of anthrax and other biowarfare agents are lateral flow test strips. These devices, which function much like home pregnancy tests, utilize antibodies that bind to specific proteins associated with particular pathogens of concern. Since different organisms express different sets of proteins, users of these antibody-based products must stock a different test strip for each of anthrax, ricin, botulinum toxin, SEB (Staphococcal Enterotoxin B), plague, etc. Moreover, since the process of raising antibodies in mammals remains slow and cumbersome, antibody based assays are difficult to manufacture in very large quantities in a short time period that may be required to respond to an unexpected bioterrorist attack.

It would therefore be desirable to have an assay that can be used by first responders to assess substances suspected of being biowarfare agents so as to rapidly and inexpensively eliminate a variety of mundane substances before more advanced testing is employed.

It would also be desirable to have an assay of the aforementioned type that can be used in conjunction with substances suspected of containing a wide range of biowarfare agents.

It would further be desirable to have an assay of the aforementioned type that can be manufactured in large quantities in a short period of time in the event of a surprise terrorist attack.

SUMMARY OF THE DISCLOSURE

The present disclosure relates to assays, methods, and kits for testing powders and other samples suspected of containing a biowarfare agent, such as pathogens and/or toxins (such as proteins) secreted thereby. According to certain provided methods, the sample is first collected by a swab or pad or the like, then immersed in or otherwise contacted with one or more reagents that produce a detectable signal (e.g., color) only in the presence of protein. Failure to produce that signal (such as a color change) indicates that the sample likely does not contain biological material, such as a pathogen or toxin. This permits the elimination of a variety of ordinary safe substances such as sugar, dry wall dust, cleaning solutions, etc. from being subjected to further testing. If it is determined that biological material (e.g., protein) likely is present in the sample, the sample may then be subjected to specific tests using antibodies or the like to determine if a particular pathogen or toxin is present.

In addition to testing for protein content, the sample in some embodiments is also tested to determine if it contains sugar, which is a common source of anthrax hoaxes and false alarms. Moreover, the sample in some embodiments is tested for pH to determine if it is either too acidic or too basic to typically sustain life or contain living material.

In one embodiment, reagents are provided in transparent tubes and the sample is collected using swabs. Separate tubes may be provided, for example, to test for protein, sugar, and/or pH.

In another embodiment, pair(s) of pads are employed that are saturated with reagents that, when combined, produce a color in the presence of protein. The sample is collected on one of the pads and sandwiched or pressed against the other pad. If it is determined that protein is present, further analysis of the sample may be performed.

In a specific example, after detection of protein in the sample, one of the pads that has been in contact with the sample is then placed in contact with a stack of membranes under conditions that permit biomolecules to be transferred from the sample to the stack. This transfer process may be carried out generally as described in U.S. patent application Ser. No. 09/718,990 filed Nov. 20, 2000 (incorporated herein by reference in its entirety). A different biomolecule may be identified on each of the membranes (if it is present in the sample), corresponding, for example, to different pathogens or toxic compounds or other biological molecules. Thus, in certain embodiments the user can determine not only that biological material is present in the sample but also which particular pathogens or toxins are present.

In yet another embodiment, an analytical test strip is employed for the analysis, the test strip having an absorbent carrier impregnated with a protein indicator. The test sample, which in this embodiment usually has been solubilized or dissolved or otherwise comprises a fluid, is brought into contact with the test strip. In those examples where the sample comprises a liquid, the liquid facilitates solubilization of the protein indicator in the absorbent carrier, therefore enabling mixing of the test sample and the indicator and generation of a detectable color change or other signal in the presence of protein. The test strip may also include sugar and pH detectors, or separate test strips for these may be provided.

Particular embodiments are provided as kits, such as field test kits that are readily employed in the field, for instance at the site of a suspected biowarfare agent or bioterrorism contamination. A positive control may also be provided in the kits, to establish that reagent(s) in the kit are functioning properly and/or that the user is following the correct procedures.

An advantage of certain embodiments is that they provide orderly systems for testing suspicious samples that allow obviously safe samples to be eliminated before sophisticated, expensive testing is involved in the analysis. It is particularly envisioned, for instance, that provided methods and kits can be used to assist in triaging possible biowarfare contamination sites and incidents, thereby permitting appropriate allocation of resources.

Another advantage of certain embodiments is that the methods can be used to identify the presence of any pathogen or toxin that includes at least one protein or peptide species, and are not limited to the detection of a particular biological agent as is seen with assays that utilize analyte-specific reagents.

In some embodiments, additional testing is carried out to determine which specific biological agent(s) is present in the sample.

A further advantage of certain embodiments disclosed herein is that protein carrier material (i.e., culture medium) can be detected in addition to the pathogen or toxin, or even in the absence of the pathogen or toxin. Carrier material is a support medium necessary for biological growth. Many biowarfare agents will be prepared and dispersed with significant amounts of carrier material present; the presence of this carrier is an additional indicator that a biological material, potentially hazardous, may be present.

These and other features, aspects, and advantages of the present invention will be better understood with regard to the following description, appended claims, and accompanying drawings.

BRIEF DESCRIPTION OF THE FIGURES

FIG. 4 is a perspective view of a pad from a kit according to certain provided embodiments, being applied to a membrane stack.

DETAILED DESCRIPTION

I. Tube Based Assay

Figure 1:
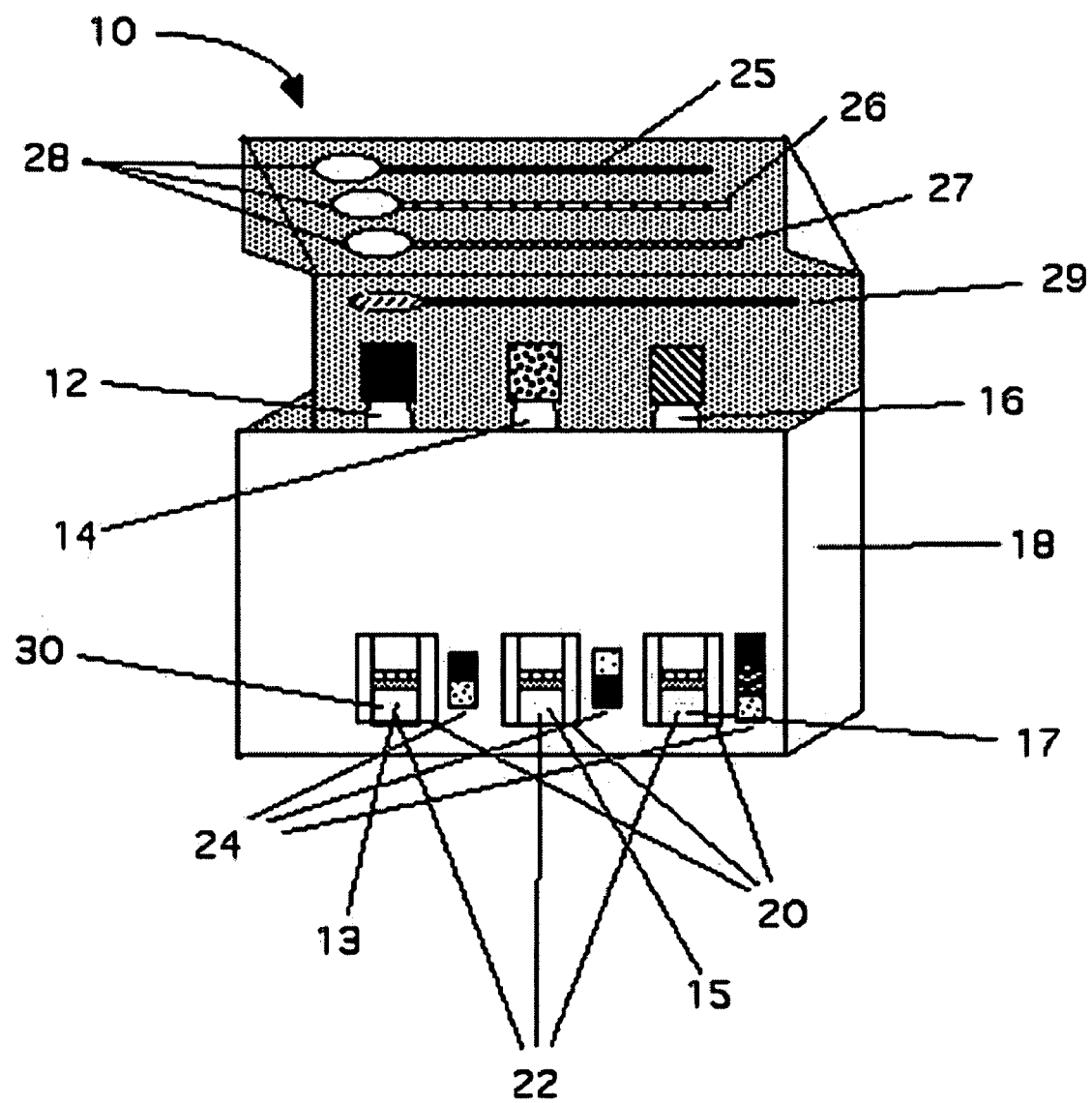
FIG. 1 is a perspective view of a kit according to one embodiment.

With reference to FIG. 1, a kit according to a first embodiment is generally designated by reference numeral 10. Kit 10 comprises a first test tube 12 for testing for the presence of proteins, an optional second test tube 14 for testing for sugars and an optional third test tube 16 for testing the pH of the sample.

The test tubes (or like reaction vessels) are received within a container 18 constructed of cardboard or the like. Windows 20 may be defined in one face of container 18 to permit the calorimetric or other detectable reactions within each tube to be visualized from outside container 18. In certain examples of kit 10, color coded markings 24 are imprinted on the outside of containers 18, for instance adjacent windows 20, to allow users to compare the color of reacted reagents 13, 15, and 17 with a standard to assist in interpretation of readings. Alternatively, tubes 12, 14 and 16 may be mounted to a carrier (e.g., as shown in FIG. 9) that is removably mounted within container 18. If such a carrier is employed, the color coded markings may be provided on the carrier rather than the container 18. In specific examples of kit 10, the tubes and carrier may be molded from plastic or the like to form an integral unit.

Swabs 25, and optionally 26 and 27, for use with each of the test tubes 12, 14, and 16 respectively, are also provided within container 18. Though it is not essential, in some examples each swab is of like construction and as shown in greater detail in FIG. 2(b) comprises an absorbent tip 28 constructed of cotton or another absorbent and generally inert material affixed to a shaft 25a which may be constructed for instance of a chemically inert material such as plastic, polyethylene or the like. Tip 28 is preferably frictionally engaged with shaft 25a rather than by adhesives that contain proteins, which may yield false positives. As described herein, each tip 28 is impregnated or saturated with a different liquid reagent. To prevent dehydration of tip 28, each of the swabs 25, 26, and 27 are optionally contained in a fluid impervious wrapper or envelope (not shown).

One of ordinary skill in the art will appreciate that the described methods can also be carried out in multi-well format. Multi-well plates in some embodiments provide the benefit of testing many samples at the same time. Non-limiting examples of commercially available multi-well plates include 4-well, 6-well, 12-well, and 24-well plates (though plates with more wells, including for instance 96 well plates are also contemplated). Multi-well plates are available, for instance, from suppliers such as Nalge Nunc International, NY, or Corning Costar, MA.

A protein control swab 29 may also be included for use with the present methods and kits, to minimize the likelihood that a negative test for protein results from failure of certain reagents in the kit (for instance, due to age of the reagents and the like, or through user error).

Protein Test

Figure 2A:
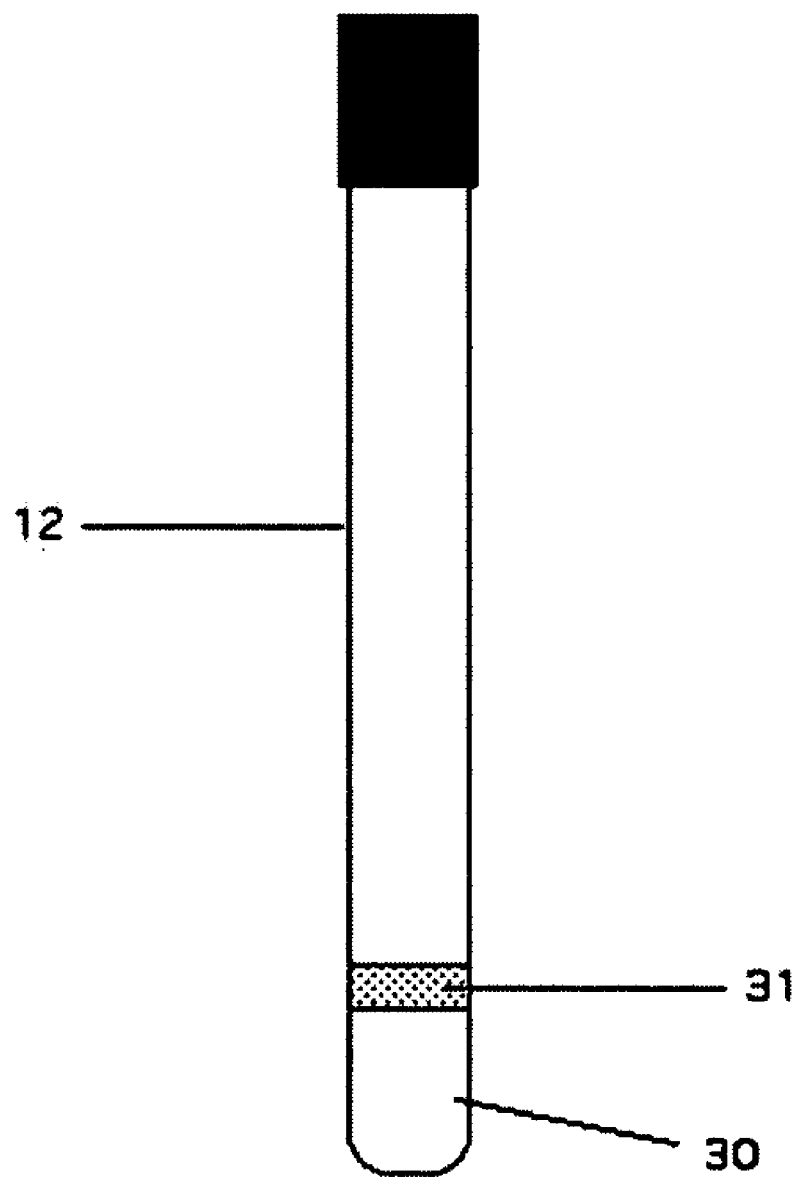
FIG. 2(a) is a front elevation view of a test tube according to certain embodiments.
Figure 2B:
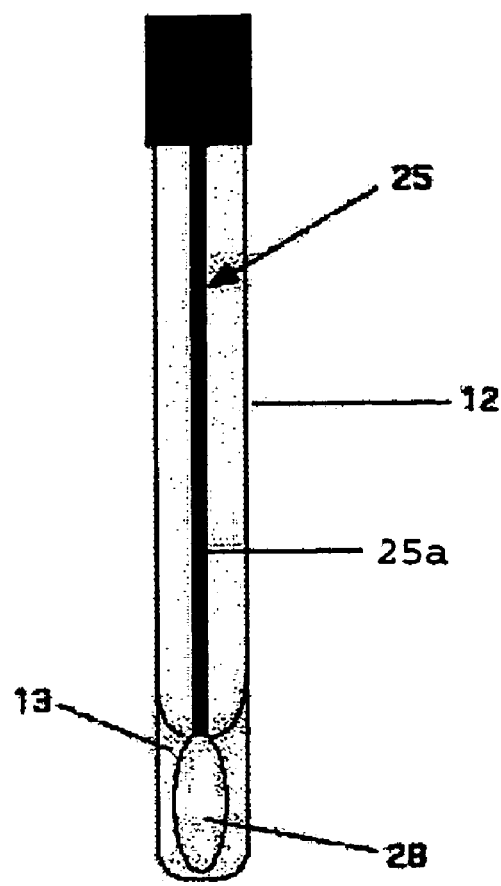
FIG. 2(b) is a front elevation view of the test tube shown in FIG. 2(a), with a swab shown inserted therein.

With reference to FIG. 2(a), first test tube 12 for testing the protein content of the test sample may be a "Snap Cap" transparent plastic tube such as those available from Falcon (35-2057). Optionally, tube 12 may be capped with a neoprene stopper such as VWR #59589-132, instead of a "Snap Cap" cap. Optionally, tube 12 may be a screw-cap vial, for example Greiner Cat.# 163-160. Example dimensions of tube 12 are about 100 mm in length and 17 mm in diameter. In a first embodiment, tube 12 of such dimensions is provided containing about 0.25 ml of bicinchoninic acid 30

(BCA; 1.0% BCA-Na$_2$, 2.0% Na$_2$CO$_3$, 0.16% NaK tartrate, 0.4% NaOH, 0.95% NaHCO$_3$, pH to 11.25 with 50% NaOH) and 0.5 ml of mineral oil 31 that floats on top of the BCA. The mineral oil increases the stability of the reagent by protecting it from any ambient contaminants, as well as by reducing or eliminating evaporation and generally reducing its exposure to the air. By way of example, BCA Protein Assay Reagent A available from Pierce (Rockford, Ill.) may be employed in tube 12. The BCA assay is described in U.S. Pat. No. 4,839,295 to Smith as well as in *Analytical Biochemistry* 150:76–85, 1985, both of which are incorporated herein by reference in their entirety. BCA is a water-soluble compound capable of forming an intense purple complex with cuprous ion (Cu$^{1+}$) in an alkaline environment. It is therefore employed for measurement of proteins, since cuprous ion is produced when protein reacts with alkaline Cu$^{2+}$ (biuret reaction). Optionally, the BCA solution is supplemented with a detergent (for example, 0.1%–1.0% w/v sodium dodecyl sulfate (SDS)), or other additives, for example bleach or lytic enzyme(s) (such as lysozyme and/or lysostaphin). The detergent or other additive(s) is believed to assist in releasing protein from the biological sample into solution, thereby facilitating detection.

With reference to FIG. 2(*b*), tube 12 is adapted to receive first swab 25. The tip of swab 25 is preferably saturated with Cu$^{2+}$ (4% CuSO$_4$0.5H$_2$O, for instance Cat# 23224 of Pierce Chemical Co.) that generates a biuret reaction with peptide bonds in the presence of protein(s).

If protein is present in the sample, it will react with the Cu$^{2+}$ to yield Cu$^{1+}$ in a biuret reaction. When a swab that has been contacted with a sample containing protein is dipped into tube 12, the Cu$^{1+}$ reacts with the BCA 30 and forms a purple complex, thereby indicating that protein is present. In general, if protein is present the sample is selected for further characterization, for instance detection or identification of one or more specific biological materials or organisms in the sample.

One or ordinary skill in the art will further appreciate that other protein assay techniques can be adapted for use with the present methods and kits, including but not limited to the Pyrogallol Red system, assays based on interaction with a fluorescent compound with binding affinity to proteins, peptides or amino acids, ultraviolet absorption, and chemiluminescence techniques. For other applicable protein detection methods, see also U.S. Pat. No. 5,981,287 to Sinclair et al., and the NanoOrange™ Protein Quantitation System available from Molecular Probes (Eugene, Oreg.).

Briefly, the Pyrogallol Red dye method involves the interaction of Pyrogallol Red-molybdate complex with protein (or a sample suspected of containing protein). The reagent can be formed by combining Pyrogallol Red (0.015 g/L), Sodium Molybdate (0.06 g/L), Succinic Acid (94.8 g/L), Sodium Benzoate (0.4 g/L), Sodium Oxalate (0.1 g/L), and methanol (10 mL/L) to form a red complex. In presence of protein, the color of the complex changes to a blue purple color with a maximum absorption at around 600 nm, which color change can be monitored either visually or using commercially available instrumentation.

Briefly, fluorescence techniques are based on the well-known principle that certain fluorophores (e.g., fluorescamine, O-pthaldialdehyde, etc.) react with primary amines of proteins resulting in the emission of fluorescence that is different from the fluorescence of the native (unbound) compound. Briefly, proteins differ in their ability to absorb ultraviolet light when exposed to it. Differences in absorption are the function of presence (and/or quantity) of certain types of amino acids (e.g., tyrosine and tryptophan). Proteins with different numbers of these amino acids will exhibit characteristic absorptions at 280 nm.

For example, fluorescamine reacts with the primary amino groups found in terminal amino acids and the amine of lysine to form fluorescent pyrrolinone type moieties. The resulting fluorescamine adduct has a maximum absorbance at 400 nm and a maximum emission peak at 460 nm. In addition, o-pthaldialdehyde, in the presence of reduced sulfhydryl groups, reacts with the primary amino groups found in terminal amino acids and the amino group of lysine to form fluorescent moieties. The resulting O-pthaldialdehyde adduct has a maximum emission peak at 460 nm. Emitted fluorescence can be measured using commercially available fluorometers. A non-limiting example of a fluorometer is the handheld fluorometer, Picofluorometer™ (Turner Designs, Sunnyvale, Calif.).

Other protein assay techniques can be adapted for use with the present methods and kits, including the Lowry and Bradford techniques known to those of ordinary skill in the art. See Bradford, *Analyt. Biochem.* 72: 248-254, 1976; and Lowry et al., *J. Biol. Chem.* 193: 265-275, 1951. Briefly, the Bradford assay involves a change in color from protein binding to Coomassie dye. The Bradford reagent can be made by dissolving 100 mg Coomassie Blue G-250 in 50 ml 95% ethanol, adding 100 ml 85% (w/v) phosphoric acid to this solution and diluting the mixture to 1 liter with water. Briefly, the Lowry assay involves a change in color from folin-phenol binding to protein. To make the relevant reagents, combine (1) Lowry reagent (Na$_2$CO$_3$ in 0.1 M NaOH) and (2) CuSO$_4$ in diH$_2$O and (3) sodium potassium tartrate (NaKC$_4$H$_4$O$_6$4H$_2$O) (98:1:1) with (4) Folin's Reagent: Phenol reagent 2N (Folin—Ciocalteau reagent), using well known procedures.

A protein control swab 29 may also be included for use with the present methods and kits, to minimize the likelihood that a negative test for protein results from failure of certain reagents in the kit (for instance, due to age of the reagents and the like, or through user error). An example of a swab that may be utilized as protein control swab 29 is Berkshire Cat. # LT003163.10. The protein control swab is coated with a protein, for example casein (Vector Laboratories, # SP-5020), for instance at a concentration of 5% w/v. Alternatively, bactotryptin, 5–50% BSA, etc., may be used as a protein control. Protein control swab 29 is adapted to be dropped into first test tube 12 by the user if the sample being tested using first swab 25 does not generate a purple complex (i.e., tests negative for protein). If the components of kit 10 are functioning properly and the user is following the proper procedure, placement of protein control swab 29 in test tube 12 should result in a reaction (i.e., a color change), since the protein on control swab 29 will react with the Cu$^{2+}$ on swab 25 to yield Cu$^{1+}$ in a biuret reaction, which then reacts with the BCA 30 and forms a purple complex (or is otherwise indicated by the protein detection system used in that method and kit, if a non-BCA system is used). Failure to produce such a complex might indicate, for example, user error, contamination of certain reagents, etc. and that the results of the test should be discarded.

In still other embodiments, kits are provided with a protein in a solid, powder, or liquid form to be employed as a positive control. Similarly, a paper strip (for instance, comprised of Whatman® Filter Paper) soaked in a protein solution (e.g., BSA or another solution) and dried down may be employed in lieu of a control swab.

It is understood that the mere presence of protein does not guarantee that the test substance contains a hazardous agent such as a biowarfare agent. For instance, the following mundane ("household") substances likely will test positive for protein, but do not on their own pose any toxic health hazard:

| *Breadcrumbs | Chili powder | Yeast |
|---|---|---|
| *Flour | Brown sugar | |
| Nutmeg | Cornmeal | |
| Cinnamon | Gelatin | |

*These materials may or may not test positive for protein

Sugar Test

Second test tube 14 optionally may be provided to test the sample for the presence of sugar. Tube 14 is, by way of example, of the same dimensions as tube 12 but is made of glass and contains 0.2 ml of 77% sulfuric acid available from Sigma (St. Louis, Mo.). Tube 14 is adapted to receive second swab 26 having an absorbent tip that is saturated with a 1% tryptophan. This solution can be prepared by dissolving 1 g of L-tryptophan (solution available from Sigma Aldridge, St. Louis, Mo.) in 100 ml of warm distilled water.

Similarly to the protein test above, a test sample can be analyzed for the presence of sugar by contacting second swab 26 with the test sample, then inserting second swab 26 into tube 14 so that second swab 26 and the sample contained thereon comes into contact with the sulfuric acid contained in tube 14. In the presence of sugar, the test reagent will turn brown; in the absence of sugar, there will be no color change. As sugar is one of the more common agents mistaken for a possible bioterrorism agent, a positive result for sugar offers further reassurance to the user that there likely is no risk present if the protein is negative and the pH neutral. If protein is positive, a positive reading for the presence of sugar provides further characterization of the suspicious substance, but further testing of the substance likely should be conducted, for instance using tests for specific pathogens.

pH Test

Third test tube 16 may be optionally provided to test for the pH of the test sample or its environment. Any of a variety of commercially available pH indicator reagents that show a color change in the presence of acid or base (i.e., litmus tests) may be employed, such as Universal pH indicator (cat # IND-V1) from Voigt Global Distributor (Kansas City, Mo.). The pH tester swab 27 is pre-wetted with distilled water. Acidic samples collected with the swab and transferred to the tube containing the pH Universal indicator reagent will yield a red color in the solution; basic samples turn blue; and neutral samples are yellow/green. Any change in color to blue or red indicates a basic or acidic pH, respectively. The pH test in and of itself does not determine the presence or absence of biological materials in the suspect sample. However, a blue or red color (or other color for other indicator substances) indicates an 'extreme' pH for biological material, and reduces the likelihood there is a threatening bioterrorism agent present even if the substance tests positive for protein.

The kit embodiment illustrated in FIG. 1 can be readily used, for example, by the hazardous materials unit of a fire department that is called out to respond to reports of suspicious powders or the like. A user first removes swab 25 from its wrapper (not shown) and collects a portion of the suspect sample on the tip of the swab. After about five seconds (sufficient time for the reagent impregnated in the tip of swab 25 to react with the sample), the swab is inserted into tube 12 and the tube can be capped. The BCA in the tube reacts with the contents carried by the swab, and yields a color reaction as discussed herein in the presence of protein.

Portions of the suspect sample also may be collected on swabs 26 and 27 in a similar manner to that described above, and the swabs inserted into tubes 14 and 18 respectively.

After sufficient time for the colors to develop (e.g., about 1–10 minutes), the user looks at the solutions in the tubes (e.g., through windows 22) and compares the color of the reagents 13, 15, and 17 with the color of color code markings 24.

If the substance tests negative for protein, this is an indication that it likely does not contain biological material (e.g., microorganisms, toxins, and so forth) and is therefore likely not a hazard. In this case, the sugar test can be used to provide further confirmation of the safety of the sample, since many false alarms are caused by sugar. The pH test can be used to provide an additional level of confirmation, by indicating that a sample is too acidic or too basic to support a microorganism. Any substance that tests positive for protein can be subjected to specific assays such as antibody tests, bacterial culture, and/or DNA testing. As stated, the source of the protein could be from, for instance, microorganisms, an endospore coat, toxins secreted by microorganism, or from culture medium used to cultivate microorganisms.

Specific examples of the provided methods primarily involve identifying the presence of protein, a biomolecule found in all living material. Toxins produced by certain disease-causing microorganisms are also proteins. All the biowarfare agents on the U.S. Centers for Disease Control's "A" list—Anthrax, Smallpox, Plague, Botulinum toxin, Tularemia, Filoviruses, and Arenaviruses—contain proteins. On the other hand, many mundane substances frequently mistaken to be potential biowarfare agents, such as powdered sugar, dry wall dust, flour, paper fiber, and many cosmetics, do not usually contain significant amounts of protein. In addition to identifying proteins, kits may include reagents to determine pH and/or the presence of sugar. These additional tests allow further characterization of the test material.

The table below contains a summary of results obtained with a tube-based kit embodiment prepared as described herein, along with the recommended interpretation and recommendation for further action.

| Sample | Protein | pH | CONCLUSION |
|---|---|---|---|
| Potentially Biohazardous material | + | Neutral (+) | Further testing recommended |
| Yeast | + | Neutral (+) | Further testing recommended |
| Sugar, cornstarch, baking powder | – | Neutral (+) | Biological threat unlikely |
| Dry wall dust, paper fiber | – | Neutral (+) | Biological threat unlikely |
| Egg white | + | Neutral (+) | Further testing recommended |
| Cleanser | – | Basic (–: turns blue) | Biological threat unlikely |

II. Pad Format

Figure 3A:
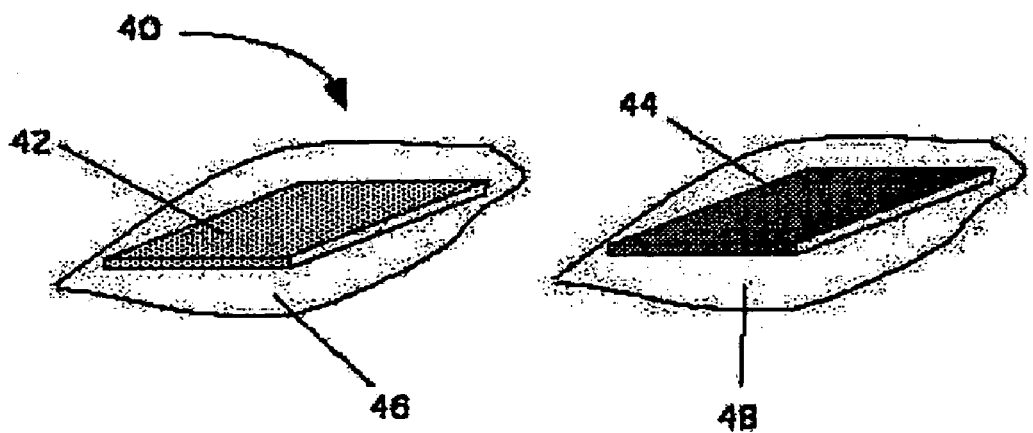
FIG. 3(a and b) are perspective views of a pad assembly kit according to certain embodiments, shown (a) with the pads separated and (b) in use.

Another embodiment of the detection kit is illustrated in FIG. 3 and is designated by reference number 40. Kit 40 in certain examples comprises a first pad 42 saturated in $Cu^{2+}$ and a second pad 44 saturated in BCA. (Alternatively swab 28 may be employed in lieu of pad 42.) The pads are constructed, for instance, of filter paper such as that available from Whatman. Each pad may be enclosed in separate fluid impermeable envelopes 46, 48. Optionally, pads or swabs may also contain one or more additives, for example detergent, bleach or lytic enzyme(s) (such as lysozyme and/or lysostaphin).

Pads 42, 44 are removed from the envelope(s) and the user wipes pad 42 across a solid surface on which a suspicious powder or other evidence of a potential biowarfare agent may be present. (If swab 28 is employed in lieu of the pad, the sample is collected in a conventional manner.) Pad 42 is then pressed against pad 44 with the sample sandwiched there between, so that the sample comes in contact with fluid from both pads. The pads are placed in an enclosure, such as a plastic bag, and squeezed together (e.g., in the palms of the user's hands). Gentle pressure is applied for about one minute to five minutes. If a purple color is evident on the pads, this indicates the sample contains protein and suggests that the sample contains a biological material that warrants additional testing for particular pathogens or toxins of concern.

Optionally, pads for detecting sugar and pH can also be provided by adapting the tube-based system described above for use in a pad format, similarly to that described for the protein test.

To specifically identify the pathogen or toxin found in the test sample, pad 42 or 44 (or another pad that has been used to collect the sample) may be applied to a membrane stack such as that described in U.S. patent application Ser. No. 09/718,990. Target capture membranes 48 (FIG. 4) are constructed of a porous membrane material that has a high affinity but a low capacity for proteins and possibly other biomolecules. Membranes of this type are sold commercially by 20/20 GeneSystems, Inc. (Rockville, Md.), for instance as part of the Multi-Replica Blotting Kit for Gels. Use of this type of membrane helps to ensure efficient presentation of the capture molecule (e.g., an antibody or other binding element) to the test sample.

In certain embodiments, each target capture membrane is provided pre-coated or loaded with a capture molecule, such as an antibody or other probe (e.g., a nucleic acid probe), which capture molecule is specific for a different pathogen (or toxin, etc). By way of example, provided membranes within one system may include binding agents for anthrax, small pox, plague, and botulism toxin (or for a particular epitope or nucleic acid sequence associated with these organisms or agents). This is a representative selection of organisms that can be detected using the provided methods and devices, and is not meant to be limiting.

Alternatively, in other embodiments the migrating biological molecules from the test sample bind to membranes in the stack that have a non-specific (i.e., ubiquitous) affinity for biomolecules (or a class of molecule, such as proteins). In these embodiments, after transfer the membranes are separated and each is incubated in a different detector molecule (e.g., a probe or antibody) specific for a different pathogen or toxin or other molecule. This method is generally analogous to the one described in the Multi-Replica Blotting Kit for Gels available from 20/20 GeneSystems, Inc. (Rockville, Md.).

In representative examples of such embodiments, the sample is transferred to a stack of about ten membranes, half of which may be used in the field for a preliminary identification of a pathogen or toxin, while the other half optionally may be preserved for confirmatory testing in a laboratory setting.

Transfer from the sample-contacted pad 42 or 44 to the membrane stack 48 takes place between two pads 50a, 50b constructed of filter paper in a fluid impervious enclosure 46.

III. Test Strip Format

Figure 5:
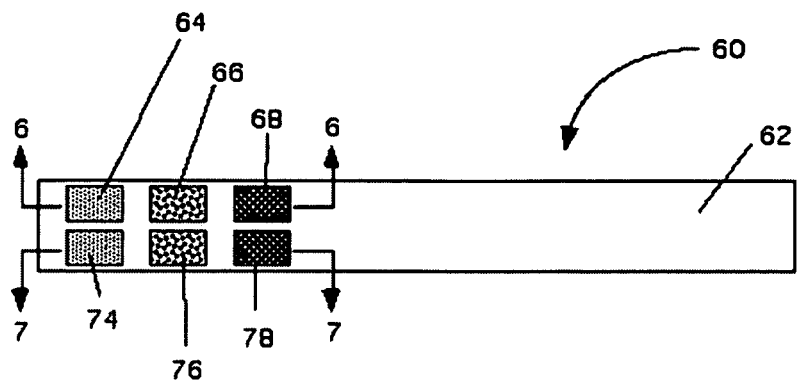
FIG. 5 is a top plan view of an analytical test strip according to certain embodiments.
Figure 6:
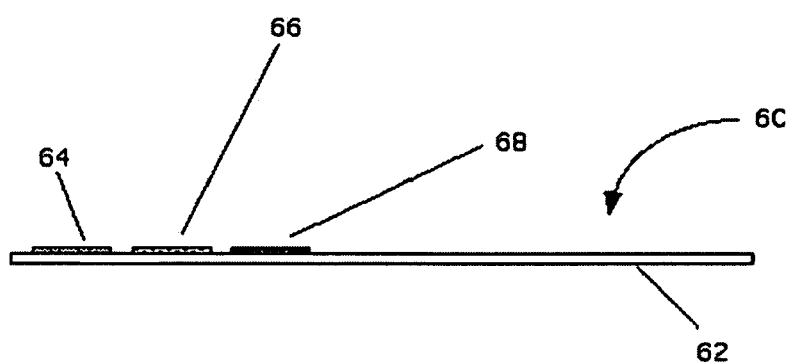
FIG. 6 is a sectional view taken along line 6—6 of the analytical test strip illustrated in FIG. 5.
Figure 7:
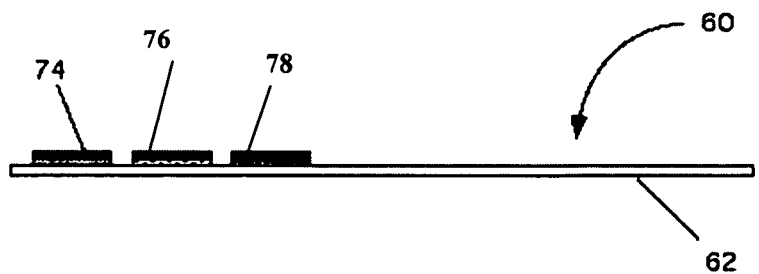
FIG. 7 is a sectional view taken along line 7—7 of the analytical test strip illustrated in FIG. 5.

In a third embodiment, illustrated in FIG. 5, an analytical test strip 60 may be employed. Test strip 60 generally comprises a carrier 62 comprised of plastic or the like having mounted thereto a plurality of absorbent pads 64 and optionally 66 and 68 for identifying the presence of protein and sugar, as well as the pH of the test sample, respectively. Absorbent pads may be constructed of filter paper, felt, or a variety of other fibrous materials. Pad 64 is separately impregnated with one part of BCA Protein Assay Reagent B and 39 parts of BCA Protein Assay Reagent A (Pierce, USA), such that the two reagents do not appreciably intermingle or interact or react with each other prior to use of the test strip. For instance, each reagent may be applied in solid form or in liquid form to different portions of pad 64 and dried thereon, such that the addition of a liquid to the pad causes solubilization and mixing of the components.

It will be appreciated by those with skill in the art that alternative protein indicators may be employed such as those described in U.S. Pat. No. 5,593,895 to Cahill et al., including Coomassie Blue and Fast Green FCF, and those systems described herein.

Similarly, pad 66 is impregnated with a suitable sugar indicator system, such as those described herein and as will be apparent to one of skill in the art.

Similarly, pad 68 is impregnated with a suitable pH detector, for instance the Universal pH Indicator (Voigt Global Distributor, Inc.) or other pH indicator known to those of ordinary skill in the art.

To use the test strip in analysis of a sample, the sample is usually either a liquid sample or a sample that has been introduced into a liquid. Optionally, one or more additives, for example detergent, bleach or lytic enzyme(s) (such as lysozyme and/or lysostaphin), can be added to the sample. For instance, if the suspect substance to be tested is a powder, a portion of the powder is collected and dissolved or suspended in water or another solvent or buffer. The test strip is then brought into contact with the sample, such that the liquid of the sample assists in solubilization of the reagents impregnated in pads 64 and optional pads 66 and 68. As with other embodiments described herein, the results are then interpreted from the test strip by comparing the colors that develop on the strip to color codes provided with the kit. Instructions are also provided for interpreting the colors.

In another scenario, reagents are placed on one pad and control samples are placed on the other. Pads are dried and put in the proximity of each other. Again, reaction will happen only after liquid medium is introduced on or around the pads.

In order to control for the occurrence of false negatives, a plurality of control pads 74, 76, and 78 may be optionally provided, either on a second test strip or on the same test strip, for instance adjacent to pads 64, 66, and 68 and of similar format. In some embodiments, each of these pads is of dual construction, such that the pad includes both the reagents necessary for detecting the substance and the substance itself. Thus, Pad 74 is impregnated with a protein preparation, such as casein or BSA or any other protein solution, as well as BCA Protein Assay Reagent A and Reagent B. Similarly, pad 76 is impregnated with a simple sugar, such as glucose, maltose, lactose, sucrose, and so forth, as well as component(s) necessary for detection of the sugar. Finally, pad 78 is impregnated with any base or acid that is available in solid form, as well as with a pH indicator. Optionally, two pads 78a and 78b (not shown) are provided, one impregnated with a base and the other with an acid, to provide bracketing controls for determination of pH. As explained above for pads 64, 66, and 68, each of pads 74, 76, and 78 are prepared in such a way that the individual components with which the pads are impregnated are not mixed or allowed to intermingle until the test in carried out. In this way, the user can watch the control samples develop concurrently with analysis of the test sample.

In another embodiment, the control reagents are placed and dried on one set of pads and the control samples are placed and dried on another set. The two sets of pads are mounted on the test strip in close proximity to each other (thus, with the protein detection reagents juxtaposed adjacent to the protein control impregnated pad and so forth), either before or after the chemicals are added to the pads. As with the embodiment described above, the controls are activated by the addition of liquid, for instance a liquid sample or another fluid such as water, which solubilizes the separately applied test reagents and controls and allows them to intermingle and provide the control signals for comparison.

In embodiments using the strip test system in which the sample is not a liquid sample, specific examples contemplate that the test strip is contacted directly with the dry sample and then a fluid is added to the test strip. For instance, the test strip can be sprayed or misted with water or another solvent or buffer.

It should be appreciated that each of the aforementioned embodiments are particularly useful to emergency personnel (police, fire, rescue, private security, etc.) that are routinely the first to respond to 911 calls from distressed citizens. While some communities and jurisdictions dispatch elite units (e.g., HAZMAT teams), specially equipped and trained to respond to suspected incidents involving chemical and biological weapons, it is often not economical or efficient to deploy these elite units when the volume of hoaxes and false alarms is high. In these cases, regular first responders can use described embodiments to screen the suspicious sample and then, if the presence protein is identified, either send the sample to a laboratory for confirmatory testing or call in a HAZMAT team or other specialists to conduct specific agent detection assays in the field. For this reason, embodiments described herein in some instances will be bundled with (provided with) protective gear such as latex gloves, a protective garment (such as a Tyvex® suit), and/or a face mask, to comprise a kit or pack for use by a first responder responding to possible terrorist incidents and the like. This kit or pack can be adapted to fit in a compartment of standard fire truck, fire engine, rescue squad, ambulance and/or the trunk of a police car, fire marshal or private security car.

EXAMPLES

Example 1

Laboratory Testing of Bio-Screening Kit with Bacteria

This example illustrates testing one embodiment of the bio-screening kit, using *E. coli* bacterial dilutions in a laboratory setting, to determine its ability to detect biomaterial.

BacStationary culture of DH5α (an *E. coli* strain) growing in LB broth (0.65 mg protein/ml; 1.51×10$^9$ cells/ml) were tested. Cell count was determined from the average of two independent counts using a hemocytometer. All work was done at room temperature on the bench.

Different dilutions of cells were prepared with PBS (phosphate buffered saline, K.D. Medical). Cell dilutions were collected in 1.6 ml microfuge tubes and spun down at 5000 rpm for 4 minutes. The supernatant was removed, and pellets were resuspended directly in 250 µl Reagent A (equivalent to biuret kit test) with or without 1% SDS added. A protein detection swab was added and the tube examined for color change after 1 minute. Cells were not washed prior to this protein measurement, mimicking real world conditions when pathogenic cells are distributed in a bioterrorism incident.

| Sample | Volume (culture & PBS) | Dilution Factor (culture / PBS) | # Cells | Result of Protein Test with SDS | without SDS |
|---|---|---|---|---|---|
| 1 | 500 µl | 0 | 7.55 × 10$^8$ | YES | YES |
| 2 | 500 µl + 500 µl | 1 in 2 | 3.79 × 10$^8$ | YES | YES |
| 3 | 80 µl + 20 µl | 1 in 5 | 1.51 × 10$^8$ | YES (FAINT) | YES |
| 4 | 50 µl + 450 µl | 1 in 10 | 7.55 × 10$^7$ | NO | NO |
| 5 | 5 µl + 495 µl | 1 in 100 | 7.55 × 10$^6$ | NO | NO |

Addition of a detergent such as SDS (believed to lyse cells and facilitate protein detection) appears to be beneficial but not essential. At 1.51×10$^8$ cells, SDS appeared to help diffuse the purple color throughout the tube, facilitating detection (and suggesting bacteria were being further lysed). This might be particularly valuable with protein detection where bacterial spores may be present. Anthrax dispersed in the terror attacks of the fall 2001 was in the form of spores.

Example 2

Laboratory Testing of Bio-Screening Kit for Triaging of Mundane Substances

This example illustrates testing one embodiment of the bio-screening kit using a wide selection of mundane, household and laboratory substances.

To further characterize the bio-identification/screening kit as a triaging device, a battery of common household and laboratory substances was assembled for testing. Each substance was tested for the presence of protein and for pH using a swab format test. The protein swab saturated with Cu$^{2+}$ containing BCA Protein Assay Reagent B was contacted with the indicated substance, and then the swab was inserted in to a PROTEIN TUBE containing 0.25 ml of BCA (BCA Protein Assay Reagent A). Simultaneously, the pH of the liquid was tested using the pH swab. After a one minute incubation at room temperature, the color of the solutions in the tubes was compared to standard color codes to interpret the results. Results are shown in Table 1.

TABLE 1

| Substance (Brand: composition detail) | Protein | pH | Positive Control | Conclusion | Class |
|---|---|---|---|---|---|
| Chromium piccolinat ([a vitamin] Solgar: free of yeast, sugar, salt, starch, corn, wheat, soy & dairy products. No artificial coloring, flavors) | Neg | Neutral | YES | Unlikely biothreat | Household |
| Cleanser (Bon Ami (has calcium carbonate)) | Neg | Basic (blue) | YES | Unlikely biothreat | Household |
| Drain Opener (Red Devil) | Neg | Basic (blue) | YES | Unlikely biothreat | Household |
| Non-dairy Creamer | Neg | Neutral | YES | Unlikely biothreat | Household |
| Agarose | Neg | Neutral | YES | Unlikely biothreat | Lab material |
| Artificial Sweetener (Sweet & Low, and Giant brand) | Neg | Neutral | YES | Unlikely biothreat | Household |
| Baby Powder (Giant) | Neg | Neutral | YES | Unlikely biothreat | Household |
| Bread crumbs | Neg | Neutral | YES | Unlikely biothreat | Household |
| Corn starch (Argo) | Neg | Neutral | YES | Unlikely biothreat | Household |
| D-Galactose | Neg | Neutral | YES | Unlikely biothreat | Lab material |
| Embossing powder (Ranger industries) | Neg | Neutral | YES | Unlikely biothreat | Household |
| Ficoll 400 | Neg | Neutral | YES | Unlikely biothreat | Lab material |
| Indubiose A45 Agarose | Neg | Neutral | YES | Unlikely biothreat | Lab material |
| Plaster wall dust | Neg | Neutral | YES | Unlikely biothreat | Household |
| Powdered Sugar | Neg | Neutral | YES | Unlikely biothreat | Household |
| Pressed powder (Physician's formula) | Neg | Neutral | YES | Unlikely biothreat | Household |
| SDS [detergent] | Neg | Neutral | YES | Unlikely biothreat | Lab material |
| Silica (may be used as an inert carrier to keep spore cultures static and moisture free; may be present in biowarfare agent preps) | Neg | Neutral | YES | Unlikely biothreat | Lab material |
| Sugar/Sucrose | Neg | Neutral | YES | Unlikely biothreat | Household |
| Salt [NaCl] | Neg | Neutral | YES | Unlikely biothreat | Household |
| Bacto Tryptone (Difco; may be present in biowarfare agent preps) | Pos | Neutral | NA | Further testing needed | Lab material |
| Bacto-Agar (Difco: may be present in biowarfare agent preps) | Pos | Neutral | NA | Further testing needed | Lab material |
| Bovine Serum Albumin ([AKA BSA] Protein widely used in research labs. MW 85 kDa; 72 amino acids) | Pos | Neutral | NA | Further testing needed | Lab material |
| Bread crumbs (Progresso: include butter) | Pos | Neutral | NA | Further testing needed | Household |
| Brown sugar (Domino) | Pos | Neutral | NA | Further testing needed | Household |
| Chili powder | Pos | Neutral | NA | Further testing needed | Household |
| Cinnamon (McCormick) | Pos | Neutral | NA | Further testing needed | Household |
| Cornmeal (Indian Head) | Pos | Neutral | NA | Further testing needed | Household |
| Yeast (dry) | Pos | Neutral | NA | Further testing needed | Household |
| Egg Albumin | Pos | Neutral | NA | Further testing needed | Lab material |
| Fish food (Tetra Bettamin: fish meal, ground brown rice, dried yeast, shrimp meal, wheat gluten, dried potato, dehulled soybean meal, fish oil, soybean oil, algae meal, lecithin, Vitamin C, artificial colors and preservatives.) | Pos | Neutral | NA | Further testing needed | Household |
| Flour, all purpose | Pos | Neutral | NA | Further testing needed | Household |
| Flour, whole wheat (Pillsbury Best: contains bran endosperm & germ) | Pos | Neutral | NA | Further testing needed | Household |
| Gelatin | Pos | Neutral | NA | Further testing needed | Household |
| Lysozyme | Pos | Acid (pink/red) | NA | Further testing needed | Lab material |
| Nutmeg (Frontier: organic) | Pos | Neutral | NA | Further testing needed | Household |

TABLE 1-continued

| Substance (Brand: composition detail) | Protein | pH | Positive Control | Conclusion | Class |
|---|---|---|---|---|---|
| Peptide 028. MW 1.8 kDa; 16 amino acids | Pos | Acid (pink/red) | NA | Further testing needed | Lab material |
| Trypsin. Protein used widely in research labs. MW: 26 kDa; 236 amino acids | Pos | Acid (pink/red) | NA | Further testing needed | Lab material |
| Yeast Extract (Difco; may be present in biowarfare agent preps) | Pos | Neutral | NA | Further testing needed | Lab material |
| Baking powder (Rumford: calcium acid phosphate, sodium bicarbonate, corn starch, sodium aluminum sulfate) | Neg | Neutral | X | Further testing needed | Household |
| Bentonite (inert carrier) | Neg | Basic (blue) | VERY faint purple | Further testing needed | Lab material |
| Cream of tartar (Spice Hunter (grape juice derivative)) | Neg | Acid | X | Further testing needed | Household |
| Glycine | Neg | Neutral | X | Further testing needed | Lab material |
| Pure Soda | Neg | Basic (blue green) | X | Further testing needed | Household |
| Tryptophan. Single amino acid | Neg | Neutral | X | Further testing needed | Lab material |
| Coffee, Instant Espresso (Medaglio D'Oro) | ?? | Neutral | NA | Further testing needed | Household |
| Coffee: Ethiopian blend | ?? | Neutral | NA | Further testing needed | Household |
| Aspirin/analgesic powders (BC Fast Pain Relief) | Neg | Acid (pink/red) | X | Further testing needed | Household |

1. 'Class' of material refers to where material can commonly be found.
2. Small peptides (of 12–16 amino acids) will test positive. Very small peptides (e.g., aspartame, a dipeptide found in some artificial sweeteners) will test negative for protein.

The results were consistent with the known protein content of the materials tested. Those materials that contained protein (e.g., yeast) produced a color change in the protein solution while those that did not contain protein (e.g., sugar) did not produce a color change. This demonstrates that the provided bio-screening kits can be used to quickly and easily analyze and rule out many mundane substances as potential threats.

Example 3

Field Tests

This example illustrates several tests of an embodiment of the bio-screening kit, used in real field conditions rather than laboratory situations, in order to test the robustness of the system. The reported results are from actual 911 emergency calls.

Figure 8:
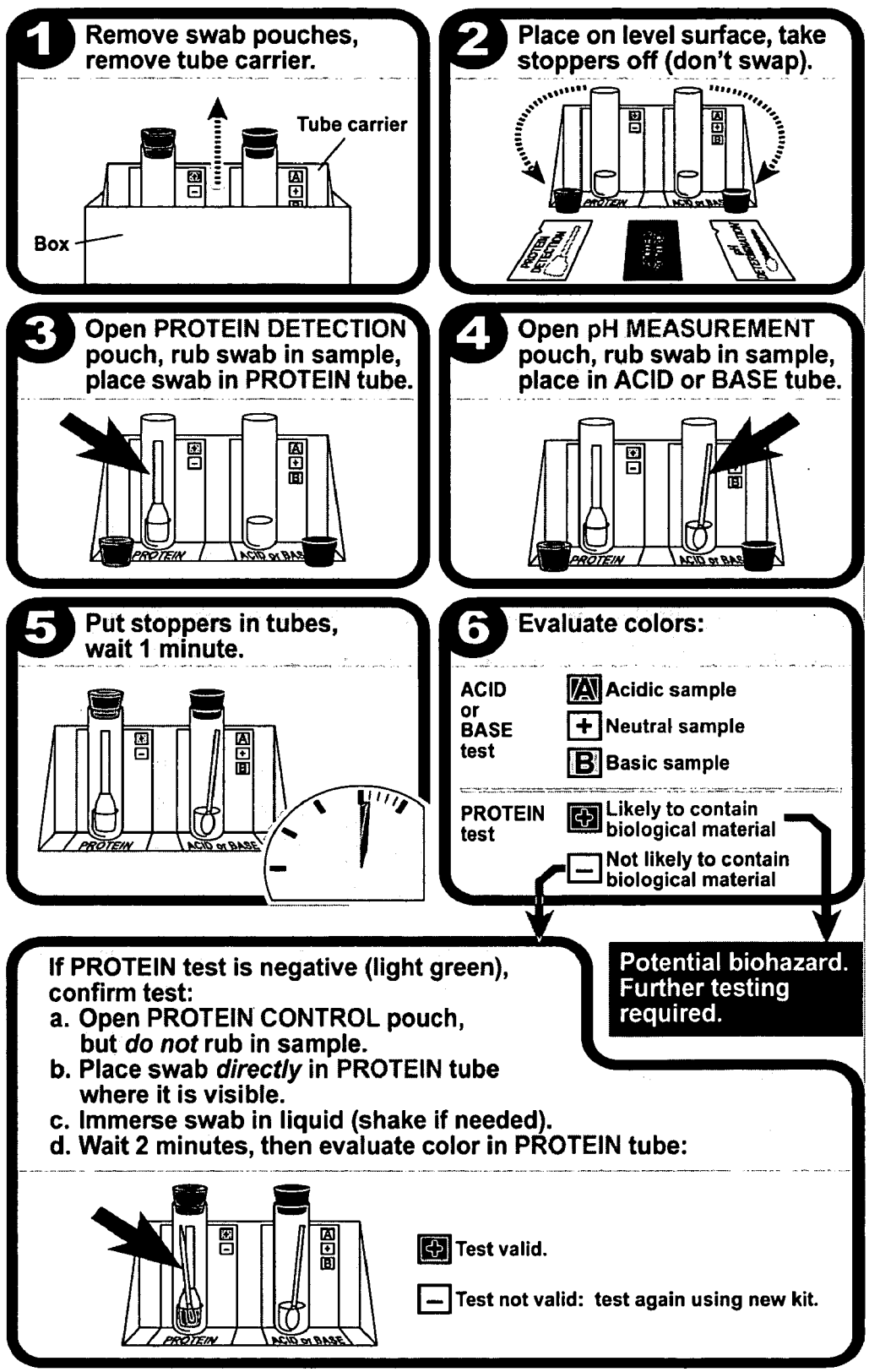
FIG. 8 is an example set of operating instructions included with one test kit in one specific embodiment.

Kits were provided to emergency response units in the Washington, D.C., area. In addition to the test components, each kit contained instructions essentially as shown in FIG. 8. It is believed that field tests were carried out in accordance with those instructions.

Samples of the suspicious materials were first collected on two swabs. Each swab was immersed in a solution that produces a color change only if the agent being tested for is present. Failure to produce a color change in the protein (green cap) tube indicates that the sample does not contain biological material, suggesting the material is most likely safe. A sample that turns solution in the pH tube (white cap) red or blue is not likely to contain biohazardous material. However this assessment should consider the circumstances in which the sample was found.

The kit also contains a protein positive control. The control consists of a third swab that is inserted into the protein tube if the test sample has not caused the solution in this tube to change color. Insertion of the positive control swab into the tube will cause the solution in the tube to turn purple. This control allows the user to confirm that when a sample is tested negative for protein, this negative result is not due to a failure of the test or user error. If it is determined that biological material may be in the sample, additional sample material may be subjected to specific tests that use antibodies or the like to determine if a particular pathogen or toxin is present. Results from these field tests are shown in Table 2.

TABLE 2

| Date | Result | Sample info |
|---|---|---|
| Jan. 5, 2002 | Negative except for pH | Coarse, whitish granular powder. 3025 V St. NE. No further testing done |
| Dec. 19, 2001 | NA | 9th Penn NW |
| Dec. 22, 2001 | NA | Mixed brown powder, ground plant material and crystals. No further testing done |
| Dec. 19, 2001 | NA | White powder coming from envelope. No further testing done |

TABLE 2-continued

| Date | Result | Sample info |
|---|---|---|
| Phone Interview Jan. 3, 2001 | All negative | 2 kits used at Bank of America; 1 with capsule (powder from an elderly woman's medicine tablet) 7 (to be) use(d) by HAZMAT team (Connecticut Ave fire house) |
| Jan. 16, 2002 | NA | White powder in envelope. Sample sent to DC gov't health dept. for further testing. |
| Jan. 25, 2002 | Negative | White powder. No further testing done. Test done at lawyer firm, Porter, Wright, Morris 1919 Pennsylvania Ave. NW |
| Feb. 3, 2001 | NA | Kit used at Gallery Place Metro (1755) |
| NA | All liquids turned brown ('?' Believe to be positive for sugar) | White powder: looked like flour. No further field tests applied to the sample; sample was sent to a lab for further testing. |
| Jan. 12, 2002 | Positive for sugar (NOTE: Older version of kit had test for sugar) | White powder. No further testing done. |
| Jan. 13, 2002 | NA (received empty box with address written on it) | 3801 Connecticut Ave. NW |
| Feb. 15, 2002 | 'Neg test' | 1901 K St. NW 13th "Ms Carrize Horn" |
| Feb. 14, 2002 | Negative protein and pH. Further tests applied include PID, APD 2000 | An unknown brown powder |
| Feb. 13, 2002 | Negative protein and neutral pH. No confirmatory testing. | 7th & Penn Ave N.W. (Metro: Archives Station) |
| Feb. 10, 2002 | Positive Protein; pH neutral | 'Powder was sugar.' 2225 5th St. NE |
| Jan. 12, 2002 Mar. 11, 2002 | Neg on P- Two neg. for protein and one faint positive. All neg. for pH. | White powdery substance 3 different sites in DC. Envelopes with similar writing. One call from field asking for assistance with test interpretation. |
| Mar. 11, 2002 | Negative protein and neutral pH. Did ADP 2000 meter. Confirmatory testing with F.B.I. | White powder |

TABLE 2-continued

| Date | Result | Sample info |
|---|---|---|
| Mar. 6, 2002 | '−' Assume this is negative for both tests. No further testing done. | Grain substance |
| Mar. 7, 2002 | Negative protein and neutral pH. No confirmatory testing. | Suspicious letter |
| NA | Negative protein and neutral pH. No confirmatory testing. | White powder on ground |
| Feb. 10, 2002 | Negative protein and neutral pH. | Sugar |
| Mar. 11, 2002 | Negative protein and neutral pH. Did ADP 2000 meter. Sent to FBI lab for further testing | White powder |
| Feb. 13, 2002 | '−' Assume this is negative for both tests. Tested VOC, pH, Rad. Nerve, blister. | White powder |
| Feb. 14, 2002 | Neg. Tested VOC, pH, Rad. Nerve, blister. | Brown powder |
| Mar. 12, 2002 | Negative protein and neutral pH. No further testing. 'Yes' to sent for further testing. | White powder substance |

This demonstrates that the present invention is useful in ruling out most of the substances that cause citizens to place emergency calls.

As of Apr. 15, 2002, >80% of field test results have been negative for protein. All users indicated that the kits functioned well and that they would recommend them.

In the course of testing and analysis, it has been determined that certain materials can be problematic in the tests. Some of these substances are listed in the following table (Table 3).

TABLE 3

Problematic Materials

| Type of material | Result | Diagnostic | Recommendation |
|---|---|---|---|
| Acidic materials (e.g., cream of tartar) | Positive control may fail | pH test will show acid by changing to a reddish color | Conduct further testing of the suspicious material |
| Reducing agents (e.g., zinc, dithiothreitol, aluminum. Baking powder which contains aluminum) | Protein test will show negative AND positive control fails | Positive control fails | Conduct further testing of the suspicious material |
| Chelating agents (e.g., EDTA, soda) | Protein test will show negative and positive control fails | Positive control fails | Conduct further testing of the suspicious material |
| Strongly especially darkly colored materials (e.g. coffee) | Can't read protein or pH tests | Test solutions turn dark making it hard to determine what if any color changes occur in tests | Conduct further testing of the suspicious material |

Example 4

Laboratory Tests for Sensitivity to Anthrax

This example provides additional laboratory screening tests of an embodiment of the bio-screening kit, used in laboratory conditions in a medical research center in Tokyo, to examine sensitivity to actual anthrax samples.

The swab from kits as described herein was contacted with liquid containing $1.4 \times 10^8$ CFU/ml anthrax, and then the swab was inserted into the PROTEIN TUBE of the kit. Simultaneously, the pH of the liquid was tested using the pH swab. After a one minute incubation at room temperature, the color of the solutions in the tubes was compared to the charts provided with the kit. All tested protein tubes showed a color change from clear to purple, indicating that protein was present. No change was observed in the pH tubes. Based on these results, in a field setting further analysis of the samples would be indicated.

Two additional tests for sensitivity to anthrax were carried out, wherein incubation times were from one to ten minutes. The results are shown in Table 4 and Table 5. The results demonstrate that the described kit was able to detect anthrax.

TABLE 4

| | First Test $1.0 \times 10^8$ CFU/ml | | |
|---|---|---|---|
| Tube No. | 1 | 2 | 3 |
| 1 minute | + | + | + |
| 5 minutes | ++ | ++ | ++ |
| 10 minutes | ++ | ++ | ++ |

TABLE 5

| | Second Test | | | | | | | | |
|---|---|---|---|---|---|---|---|---|---|
| | $1.0 \times 10^8$ CFU/ml | | | $1.0 \times 10^7$ CFU/ml | | | $1.0 \times 10^6$ CFU/ml | | |
| Tube No. | 1 | 2 | 3 | 1 | 2 | 3 | 1 | 2 | 3 |
| 1 minute | − | − | − | − | − | − | − | − | − |
| 5 minutes | + | + | + | ± | ± | ± | − | − | − |
| 10 minutes | ++ | ++ | ++ | + | + | + | ± | ± | ± |

Example 5

Laboratory Testing of Bio-Screening Kit with Bacterial Spores

This example provides further illustrations of the sensitivity of an embodiment bio-screening kit to detect bacterial spores.

Additional laboratory testing of the bio-identification kit was carried out by an independent, nationally recognized testing laboratory using *Bacillus thuringiensis* (BT) spores. BT spores are a commonly used stimulant of anthrax with similar physical composition and protein content. The BT stimulant is frequently used in evaluation of anthrax tests to minimize the need for expensive, complicated safety procedures required with anthrax bacteria. Two preparations were used, a "clean" preparation and a "dirty" preparation. In general, for both preparations, a bacterial broth culture was grown to sporulation. Following growth, the dirty spore preparation was concentrated by centrifugation, resuspended, and lyophilized. The clean spore preparation was prepared by washing the spores three times with sterile distilled water prior to concentration by centrifugation and subsequent lyophilization. The dirty spore preparation mimics likely preparations of bio-active anthrax, which will contain protein from the medium used to cultivate the bacteria. The results obtained using the two categories of *Bacillus thuringiensis* spores are shown in Table 6.

TABLE 6

| Sample Type* | Kit Results | Document Appearance of Result |
|---|---|---|
| Clean Spores Iteration #1 | Positive | A bright purple color appeared as soon as the indicator swab was inserted into test tube. |
| Clean Spores Iteration #2 | Positive | A bright purple color appeared as soon as the indicator swab was inserted into test tube. |
| Clean Spores Iteration #3 | Positive | A bright purple color appeared as soon as the indicator swab was inserted into test tube. |
| Dirty Spores Iteration #1 | Positive | A bright purple color appeared as soon as the indicator swab was inserted into test tube. |
| Dirty Spores Iteration #2 | Positive | A bright purple color appeared as soon as the indicator swab was inserted into test tube. |
| Dirty Spores Iteration #3 | Positive | A bright purple color appeared as soon as the indicator swab was inserted into test tube. |
| Control | Positive | A light purple color appeared as soon as both the protein indicator swab and the control swab were inserted into the protein tube. |

*Approximately $1 \times 10^7$ spores.

Both clean and dirty spore preparations tested positive for the presence of protein using the bio-identification test kit.

Following the initial testing of the bio-identification kit with bacterial spores, inoculum levels were verified to insure that spore concentration was within a target concentration level of $10^7$–$10^8$. The results are shown in Table 7.

TABLE 7

| | Verification of Inoculum Levels | | | | |
|---|---|---|---|---|---|
| Sample Type | Dilutions Plated (CFU/plate) | | | Average CFU/plate | Average CFU/mL |
| | $10^{-5}$ | $10^{-6}$ | $10^{-7}$ | | |
| Clean #1 | 33, 37, 41 | 7, 4, 5 | 0, 1, 3 | 39 | $5.8 \times 10^6$ |
| Clean #2 | 82, 75, 71 | 18, 13, 11 | 9, 3, 4 | 76 | |
| Dirty #1 | 129, 107, 136 | 12, 9, 7 | 3, 1, 0 | 124 | $1.3 \times 10^7$ |
| Dirty #2 | 128, 157, 140 | 15, 13, 11 | 2, 1, 2 | 142 | |

The verification of the spore inoculum level indicated that the dirty spore preparation was within the target concentration level of $10^7$–$10^8$. As the average CFU/ml was slightly less with the clean spores than the target inoculum level, samples Clean #1 and Clean #2 were enumerated again using a 0.05% Triton X+PBS solution. The use of a Triton X solution was to break up clumping that can occur in clean spore preparations. The results are shown in Table 8.

TABLE 8

Second Test of Clean Spore Samples

| Sample Type | Dilutions Plated (CFU/plate) | | | Average CFU/plate | Average CFU/ml |
|---|---|---|---|---|---|
| | $10^{-5}$ | $10^{-6}$ | $10^{-7}$ | | |
| Clean #1 | 118, 87, 108 | 22, 18, 20 | 2, 0, 4 | 104 | $1.1 \times 10^7$ |
| Clean #2 | 110, 115, 101 | 19, 23, 25 | 0, 3, 1 | 109 | |

Results from the second test of the clean spore preparations indicate that the initial concentration of the spores was within the target concentration of $10^7$–$10^8$.

Additional tests for sensitivity to bacterial spores were carried out, wherein incubation times were from five to ten minutes. An inoculum volume of 100 μl directly added to the bottom of the kit test tube diluted the protein detection solution, resulting in a false negative reaction. A second test using an inoculation volume of 10 μl was carried out. The results are shown in Table 9.

TABLE 9

| Sample Type | Dilution (number of spores)* | Kit Results | Appearance of Result |
|---|---|---|---|
| Clean #1 | $10^6$ | Positive | A distinct purple color appeared after approximately 5 minutes. |
| Clean #2 | $10^6$ | Positive | A distinct purple color appeared after approximately 5 minutes. |
| Clean #3 | $10^6$ | Positive | A distinct purple color appeared after approximately 5 minutes. |
| Clean #1 | $10^5$ | Positive | A light purple color appeared after approximately 8 minutes. |
| Clean #2 | $10^5$ | Positive | A light purple color appeared after approximately 8 minutes. |
| Clean #3 | $10^5$ | Positive | A light purple color appeared after approximately 8 minutes. |
| Clean #1 | $10^4$ | Negative | No color change was observed after the 10 minute time period. |
| Clean #2 | $10^4$ | Negative | No color change was observed after the 10 minute time period. |
| Clean #3 | $10^4$ | Negative | No color change was observed after the 10 minute time period. |
| Dirty #1 | $10^6$ | Positive | A distinct purple color appeared after approximately 5 minutes. |
| Dirty #2 | $10^6$ | Positive | A distinct purple color appeared after approximately 5 minutes. |
| Dirty #3 | $10^6$ | Positive | A distinct purple color appeared after approximately 5 minutes. |
| Dirty #1 | $10^5$ | Positive | A light purple color appeared after approximately 8 minutes. |
| Dirty #2 | $10^5$ | Positive | A light purple color appeared after approximately 8 minutes. |
| Dirty #3 | $10^5$ | Positive | A light purple color appeared after approximately 8 minutes. |
| Dirty #1 | $10^4$ | Negative | No color change was observed after the 10 minute time period. |
| Dirty #2 | $10^4$ | Negative | No color change was observed after the 10 minute time period. |
| Dirty #3 | $10^4$ | Negative | No color change was observed after the 10 minute time period. |

*Number of spores.

Results from the test indicate that the detection level of this embodiment of the bio-identification kit is approximately $10^5$ bacterial spores.

It will be apparent that the precise details of the methods, kits, and compositions described may be varied or modified without departing from the spirit of the described invention. We claim all such modifications and variations that fall within the scope and spirit of the claims below.

What is claimed is:

1. An on-site triage procedure for testing a substance suspected of containing a biowarfare agent, the procedure comprising:
   providing personnel to the site of the substance suspected of containing a biowarfare agent;
   providing a kit comprising at least one protein detection reagent;
   collecting a sample of the substance; and
   testing the sample at or near the site for the presence of protein using the at least one protein identification reagent in the kit;
   wherein detecting protein in the sample indicates that the substance may contain a biowarfare agent, and wherein a substance that may contain a biowarfare agent is subjected to additional testing for at least one specific pathogen or toxin selected from the group consisting of anthrax, ricin, botulinum toxin, Staphococcal Enterotoxin B (SEB), plague, and mixtures of two or more thereof, and if no protein is detected, no further testing for said biowarfare need be done on the sample.

2. The procedure according to claim 1, wherein the at least one protein detection reagent generates a detectable color change in the presence of protein.

3. The procedure according to claim 1, wherein the kit further includes a reagent that produces a color in the presence of sugar.

4. The procedure according to claim 1, wherein the protein identification reagent is selected from the group consisting of Coomassie blue, Pyrogallol Red, fluorescamine and O-pthaldialdehyde.

5. The procedure according to claim 1, wherein collecting the sample comprises using an absorbent member impregnated with $Cu^{2+}$; and
   the at least one reagent comprises BCA.

6. The procedure of claim 1, wherein collecting the sample comprises using a porous pad.

7. The procedure according to claim 1, wherein the kit comprises:
   protein identification reagents comprising $Cu^{2+}$ and BCA;
   a swab for receiving a sample of the suspected substance, the swab being impregnated with $Cu^{2+}$;
   a container for the BCA, the container adapted to receive the swab containing the sample to determine whether protein is present depending on the presence or absence of a color change within the container.

8. The procedure according to claim 7, wherein the kit further includes a sealed container enveloping the swab to reduce dehydration of the $Cu^{2+}$.

9. The procedure according to claim 1, wherein the protein identification reagent is in the form of a test strip.

10. The procedure claim 9, wherein the test strip includes one or more reagent-carrying pads for detecting protein in the sample collected.

11. The procedure according to claim 1, further comprising testing the substance for its pH.

12. The procedure according to claim 11, wherein the kit further includes:
   (i) a reagent for determining whether the sample is of a physiological pH and
   (ii) a protein sample to serve as a control to minimize the likelihood of false negatives.

13. The procedure of claim 1, wherein at least one of the protein identification reagents is carried by a pad that is positioned in a sealed container to reduce dehydration.

14. The procedure of claim 13, wherein the at least one protein detection reagent comprises $Cu^{2+}$ and BCA.

15. The procedure of claim 14, wherein the kit further includes a plurality of reagent-carrying pads.

16. The procedure of claim 13, wherein the pad is also used to collect a powder sample.

17. The procedure of claim 16, wherein the collected powder is placed between opposing pads treated with the reagents.

18. The procedure of claim 17, wherein the at least one protein detection reagent comprises $Cu^{2+}$ and BCA.

19. An on-site triage procedure for testing a substance suspected of containing a biowarfare agent, the procedure comprising:
   providing personnel at the site of the suspected substance;
   providing a kit comprising at least one calorimetric protein detection reagent;
   collecting a sample of the substance; and
   testing the substance at or near the site for the presence of protein using the reagent in the kit;
   wherein detecting protein in the sample indicates that the substance may contain a biowarfare agent, and wherein a substance that may contain a biowarfare agent is subjected to additional testing for at least one specific pathogen or toxin selected from the group consisting of anthrax, ricin, botulinum toxin, Staphococcal Enterotoxin B (SEB), plague, and mixtures of two or more thereof, and if no protein is detected, no further testing for said biowarfare need be done on the sample.

20. The procedure according to claim 19, wherein the kit further includes a pH detector, and the procedure further comprises testing the substance for its pH.

21. The procedure according to claim 20, wherein the kit further includes:
   (i) a reagent for determining whether the sample is of a physiological pH and
   (ii) a protein sample to serve as a control to minimize the likelihood of false negatives.

22. The procedure according to claim 19, wherein the kit comprises:
   protein identification reagents comprising $Cu^{2+}$ and BCA;
   a swab for receiving a sample of the suspected substance, the swab being impregnated with $Cu^{2+}$;
   a container for the BCA, the container adapted to receive the swab containing the sample to determine whether protein is present depending on the presence or absence of a color change within the container.

23. The procedure according to claim 22, wherein the kit further includes a sealed container enveloping the swab to reduce dehydration of the $Cu^{2+}$.

* * * * *